US011174521B2

(12) United States Patent
Finegold et al.

(10) Patent No.: US 11,174,521 B2
(45) Date of Patent: Nov. 16, 2021

(54) **METHOD OF DIAGNOSIS AND TREATING GASTROINTESTINAL AND NEUROLOGICAL DISEASES ASSOCIATED WITH SPECIES OF GENUS *CLOSTRIDIUM***

(71) Applicant: The United States Government as Represented by the Department of Veterans Affairs, Washington, DC (US)

(72) Inventors: Sydney M. Finegold, Los Angeles, CA (US); Paula Carlson, Los Angeles, CA (US)

(73) Assignee: The United States Government as represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 16/409,334

(22) Filed: May 10, 2019

(65) Prior Publication Data

US 2020/0071747 A1    Mar. 5, 2020

Related U.S. Application Data

(62) Division of application No. 15/641,035, filed on Jul. 3, 2017, now abandoned.

(60) Provisional application No. 62/357,549, filed on Jul. 1, 2016.

(51) Int. Cl.
*C12Q 1/689* (2018.01)
*C12Q 1/6883* (2018.01)

(52) U.S. Cl.
CPC .......... *C12Q 1/689* (2013.01); *C12Q 1/6883* (2013.01); *C12Q 2600/106* (2013.01); *C12Q 2600/118* (2013.01); *C12Q 2600/158* (2013.01)

(58) Field of Classification Search
CPC ........ C12Q 2600/118; C12Q 2600/158; C12Q 2600/106; C12Q 1/6883; C12Q 1/689
See application file for complete search history.

(56) References Cited

U.S. PATENT DOCUMENTS

| 4,303,646 | A | 12/1981 | Cavalieri et al. |
| 4,328,316 | A | 5/1982 | Cavalieri et al. |
| 4,427,656 | A | 1/1984 | Cavalieri et al. |
| 5,539,087 | A | 7/1996 | Restelli et al. |
| 5,925,550 | A | 7/1999 | Lancini et al. |
| 2008/0254009 | A1* | 10/2008 | Finegold .............. A61K 35/745 424/93.41 |

OTHER PUBLICATIONS

Martirosian et al., (Anaerobe. Feb. 2011;17(1):43-5. doi: 10.1016/j.anaerobe.2010.12.003. Epub Dec. 16, 2010) (Year: 2010).*

(Continued)

*Primary Examiner* — Jana A Hines
(74) *Attorney, Agent, or Firm* — Ballard Spahr LLP (57) ABSTRACT

The invention includes a method of diagnosis and treating autism associated with an overgrowth of beta2-toxin-gene-positive *Clostridium perfringens* in the gut of an autistic subject. In one embodiment, the method comprises administering to the subject (e.g. a subject having an overgrowth of beta2-toxin-gene-positive *Clostridium perfringens* in the gut) one or more agents to reduce or eliminate beta2-toxin-gene positive *Clostridium perfringens* in the subject so as to relieve one or more symptoms of autism.

16 Claims, 3 Drawing Sheets

Specification includes a Sequence Listing.

Outline of the studies

(56) References Cited

OTHER PUBLICATIONS

Van Asten et al., (Veterinary Microbiology vol. 136, Issues 3-4, May 12, 2009, pp. 411-412). (Year: 2009).*
U.S. Appl. No. 15/641,035, filed Jul. 3, 2017, Sydney M. Finegold.
Arena et al. Barley 11-Glucans-Containing Food Enhances Probiotic Performances of Beneficial Bacteria. (2014) International Journal of Molecular Sciences 15 (2): 3025-3039.
Benson DA, Kars I, Lipman DJ, Ostell J, Rapp BA, Wheeler DL. GenBank. Nucleic Acid Res 2000; 30:15-18.
Carman, R.J., et al. Clostridium perfringens toxin genotypes in the feces of Healthy North Americans, Anaerobe. Apr. 2008; 14(2): 102-108.
Cornier et al., Dosage titration of a characterized competitive exclusion culture to inhibit *Salmonella* colonization in broiler chickens during growout. J. Food Prot. 61(7):796-801 (1998).
Corner et al., Treatment of Commercial Broiler Chickens with a Characterized Culture of Cecal Bacteria to Reduce *Salmonellae* Bacteria. Poult Sci. 74(7):1093-1011 (1995).
Corrier et al., Control of *Salmonella typhimurium* Colonization in Broiler Chickswith a Continuous-Flow Characterized Mixed Culture of Cecal Bacteria. Poult Sci. 74(6): 916-24 (1995).
Finegold SM, et al., Gastrointestinal microflora studies in late-onset autism. Clin Infect Dis 2002;35 (Suppl. 1):S6-S16.).
Finegold SM. Therapy and epidemiology of autism—clostridial spores as key elements. Medical hypotheses 2008;70:508-511.
Fisher DJ. Clostridium perfringens beta2 toxin: a potential accessory toxin in gastrointestinal diseases of humans and domestic animals. Theses. 2006. University of Pittsburgh.
Fisher DJ, et al., Association of beta2 toxin production with Clostridium perfringens type A human gastrointestinal disease isolates carrying a plasmid enterotoxin gene. Molecular Microbiology 2005;56:747-762.
Garmory HS, Occurrence of Clostridium perfringens b2-toxin amongst animals, determined using genotyping and subtyping PCR assays. Epidemiol. Infect. 2000; 124,61-67.
Gibson GR and Roberfroid MG, Dietary Modulation of the Human Colonic Microbiota: Introducing the Concept of Prebiotics. (1995) J Nutr. 125 (6): 1401-1412.
Giber M, Jolivet-Reynaud C, Popoff MR. Beta2 toxin, a novel toxin produced by Clostridium perfringens. Gene. Dec. 5, 1997;203(1):65-73.
Gomez et al. Purification, Characterization, and Prebiotic Properties of Pectic Oligosaccharides from Orange Peel Wastes. (2014) Journal of Agricultural and Food Chemistry 62 (40): 9769-9782.
Goossens et al. Toxin-neutralizing antibodies protect against Clostridium perfringens-induced necrosis in an intestinal loop model for bovine necrohemorrhagic enteritis. BMC Veterinary Research (2016)12:101 p. 1-8.
Harrison B, et al., . Molecular characterization of Clostridium perfringens isolates from humans with sporadic diarrhea: evidence for transcriptional regulation of the beta2-toxin-encoding gene. Applied and Environmental Microbiology 2005;71: 8362-8370.
Hume et al., Effect of a characterized continuous-flow culture of cecal bacteria of *Salmonella typhimurim* crop colonization in broiler chicks. Avian Dis. 40(2):391-7 (1996).
Hume et al., Early *Salmonella* challenge time and reduction in chick cecal colonization following treatment with a characterized competitive exclusion culture. J. Food Prot. 61(6):673-6 (1998).
Higgins D, Thompson J, Gibson T, Thompson JD, Higgins DG, Gibson TJ. Clustal W: improving the sensitivity of progressive multiple sequence alignment through sequence weighting, position-specific gap penalties and weigh matrix choice. Nucleic Acid Res 1994;22:4673-4680.
Jain et al., Xylooligosaccharides: an economical prebiotic from agroresidues and their health benefits. (2015) Indian Journal of Experimental Biology 53 (3): 131-142.
Kelly GS, Large Arabinogalactan: Clinical Relevance of a Novel Immune-Enhancing Polysaccharide (1999) Alternative Medicine Review 4 (2): 96-103.
Mayer et al. Gut Microbes and the Brain: Paradigm Shift in Neuroscience. The Journal of Neuroscience, Nov. 12, 2014, 34(46):15490-15496.
Meer RR, Songer JG. Multiplex polymerase chain reaction assay for genotyping Clostridium perfringens. Am J Vet Res. Jul. 1997;58(7):702-5.
Maidak BL, et al., The RDP-II (Ribosomal Database Project). Nucleic Acid Res 2001;29:173-174.
Morales et al., Complete genome sequence of the podoviral bacteriophage ctCP24R, which is virulent for Clostridium perfringens. Arch. Virol. 2012; 157:769-772 [PubMed: 222189671), OCPV4, OZP2, and cl)CP7R.
Parenti et al.; Ramoplanin: a review of its discovery and its chemistry. Drugs Exp Clin Res 16(9):451-5 (1990).
Popoff MR, Poulain B. Bacterial toxins and the nervous system: neurotoxins and multipotential toxins interacting with neuronal cells. Toxins 2010;2:683-737.
Rumah KR, Linden J, Fischetti VA, Vartanian T. (2013). Isolation of Clostridium perfringens Type B in an Individual at First Clinical Presentation of Multiple Sclerosis Provides Clues for Environmental Triggers of the Disease. Plos One, 8, e76359.
Ramesh et al., Prevention of Clostridium difficile-induced ileocecitis with Bacteriophage. Anaerobe 5:69-78 (1999).
Roberfroid MB; Prebiotics: The Concept Revisited (2007) J Nutr. 137 (3 Suppl 2): 830S-7S.
H. Saito, et al., Monoclonal antibodies against alpha toxin of Clostridium perfringens. FEMS Microbiology Letters (1989), 59:173-176; US Biological.
Sandler RH, et al.,Short-term benefit from oral vancomycin treatment of regressive-onset autism. J Child Neurol 2000;15:429-435.
Song Y, Liu C, Finegold S.M. Real-time PCR quantitation of clostridia in feces of autistic children. Appl Environ Microbiol 2004;70:6459-6465.
Seal et al., Characterization of bacteriophages virulent for Clostridium perfringens and identification of phage lytic enzymes as alternatives to antibiotics for potential control of the bacterium. Poult Sci. 2013; 92(2): 526-533.
Seal et al., Clostridium perfringens bacteriophages d)CP390 and cbCP26F: genomic organization and proteomic analysis of the virions. Arch. Virol. 2011; 156:25-35 [PubMed: 20963614].
Volozhantsev et al., The genome sequence and proteome of bacteriophage cPCPVI virulent for Clostridium perfringens. Virus Res. 2011; 155:433-439 [PubMed: 21144870].
Volozhantsev et al., Molecular Characterization of Podoviral Bacteriophage Virulent for Clostridium perfringens and Their Comparison with Members of the Picovirinae. PLoS ONE. 2012; 7:e38283 [PubMed: 22666499].
Wooley et al., Inhibition of *Salmonella typhimurium* in the chicken intestinal tract by a transformed avirulent avian *Escherichia coli*. Avian Dis. 43(2):245-50, (1999).
Zaman et al., The potential of resistant starch as a prebiotic, Critical Reviews in Biotechnology: (2016); 36(3): 578-584.
Zeng et al. The Generation and Characterization of Recombinant Protein and Antibodies of Clostridium perfringens Beta2 Toxin. Journal of Immunology Research, vol. 2016, Article ID 570868; Novus Biologicals.
Restriction/Election dated May 8, 2018 by the USPTO for U.S. Appl. No. 15/641,035, filed Jul. 3, 2017 and published as US 2018/0002741 A1 on Jan. 4, 2018 (Inventor—Sydney M. Finegold) (10 Pages).
Response to Restriction/Election dated Aug. 7, 2018 to the USPTO for U.S. Appl. No. 15/641,035, filed Jul. 3, 2017 and published as US 2018/0002741 A1 on Jan. 4, 2018 (Inventor—Sydney M. Finegold) (11 Pages).
Non Final Rejection dated Sep. 5, 2018 by the USPTO for U.S. Appl. No. 15/641,035, filed Jul. 3, 2017 and published as US 2018/0002741 A1 on Jan. 4, 2018 (Inventor—Sydney M. Finegold) (15 Pages).
Response to Non Final Rejection dated Feb. 4, 2019 to the USPTO for U.S. Appl. No. 15/641,035, filed Jul. 3, 2017 and published as US 2018/0002741 A1 on Jan. 4, 2018 (Inventor—Sydney M. Finegold) (15 Pages).

(56) References Cited

OTHER PUBLICATIONS

Final Rejection dated Apr. 11, 2019 by the USPTO for U.S. Appl. No. 15/641,035, filed Jul. 3, 2017 and published as US 2018/0002741 A1 on Jan. 4, 2018 (Inventor—Sydney M. Finegold) (18 Pages).

* cited by examiner

FIG. 1. Outline of the studies

FIG. 2. Spearman's rank correlation of *C. perfringens* CFU/g and the CFU/g of beta2-toxin-producing *C. perfringens* presented in log 10 scale blue= autism, red=control, log (value + 100). Spearman's corr = 0.7125 showing moderate, positive correlation.

Figure 3. *Clostridium perfringens* toxin PCR on autistic subjects. 1, MW marker; 2-12, *C. perfringens* beta2-toxin (12=ATCC 3626)

METHOD OF DIAGNOSIS AND TREATING GASTROINTESTINAL AND NEUROLOGICAL DISEASES ASSOCIATED WITH SPECIES OF GENUS *CLOSTRIDIUM*

CROSS-REFERENCE TO RELATED APPLICATIONS

This application is a Divisional of U.S. application Ser. No. 15/641,035, filed on Jul. 3, 2017, which claims the benefit of U.S. Provisional Application No. 62/357,549, filed on Jul. 1, 2016, the contents of which are herein incorporated by reference in their entireties.

Throughout this application, various publications are referenced. The disclosures of these publications in their entireties are hereby incorporated by reference into this application in order to more fully describe the state of the art to which this invention pertains.

REFERENCE TO SEQUENCE LISTING

This Sequence Listing submitted on Nov. 21, 2019 as a text file named "37759_0130U2_ST25.txt," created on Nov. 20, 2019, and having a size of 1,109 bytes is hereby incorporated by reference pursuant to 37 C.F.R. § 1.52(e)(5).

BACKGROUND OF THE INVENTION

It was known that intestinal clostridia contribute to the clinical picture of autism (U.S. Pat. No. 9,168,275). For example, our microbiological studies revealed a higher incidence and higher counts of clostridia in autism subjects' fecal samples compared to control samples and there is a significantly reduced overall bacterial diversity in the feces of the autistic group children (1-4).

Now we have discovered that autistic children may harbor an overgrowth of beta2-toxin-gene-positive *Clostridium perfringens* in their intestinal microflora and that such toxin-producing organisms are an important target to alleviate autism and its symptoms. This discovery provides additional methods for diagnosis and treating autistic children positive for toxin-producing *Clostridium perfringens* in their gut.

SUMMARY OF THE INVENTION

The invention includes a method of treating autism associated with an overgrowth of beta2-toxin-gene-positive *Clostridium perfringens* in the gut of an autistic subject. In one embodiment, the method comprises administering to the subject having an overgrowth of *Clostridium perfringens* positive for beta2-toxin gene one or more agents to reduce or eliminate beta2-toxin-gene positive *Clostridium perfringens* in the subject so as to relieve one or more symptoms of autism; thereby, treating autism associated with an overgrowth of beta2-toxin-gene-positive *Clostridium perfringens* in the autistic subject. In another embodiment, the method comprises administering to the subject (e.g. a subject having an overgrowth of beta2-toxin-gene-positive *Clostridium perfringens* in the gut) one or more agents to reduce or eliminate beta2-toxin-gene positive *Clostridium perfringens* in the subject so as to relieve one or more symptoms of autism.

In another embodiment, the method comprises a) determining an overgrowth of *Clostridium perfringens* positive for beta2-toxin gene in a sample from the subject; and (b) administering to the subject, who has been determined to have the overgrowth of *Clostridium perfringens* positive for beta2-toxin gene in (a), one or more agents to reduce or eliminate beta2-toxin-gene positive *Clostridium perfringens* in the subject so as to relieve one or more symptoms of autism.

DETAILED DESCRIPTION OF THE INVENTION

The invention includes methods of treating autism associated with an overgrowth of beta2-toxin-gene-positive *Clostridium perfringens* in the gut of an autistic subject. In one embodiment, the method comprises administering to the subject (e.g., a subject having an overgrowth of beta2-toxin-gene-positive *Clostridium perfringens* in the gut) one or more agents to reduce or eliminate beta2-toxin-gene positive *Clostridium perfringens* in the subject so as to relieve one or more symptoms of autism. Examples of symptoms of autism include, but are not limited to, social deficits, language impairment, and repetitive behaviors. Additional examples include associated neurological issues such as sleep deficits, mood swings, anxiety, hyperactivity, immune dysfunction, and seizures. Autism associated with an overgrowth of beta2-toxin-gene-positive *Clostridium perfringens* includes early onset autism, late onset autism, and regressive autism. In one embodiment, autism associated with an overgrowth of beta2-toxin-gene-positive *Clostridium perfringens* is regressive autism.

In one embodiment, feces, fecal specimen or stool may be used to determine an overgrowth of beta2-toxin-gene-positive *Clostridium perfringens* strain, *Clostridium perfringens* species or *Clostridium* genus in the gut of a subject. In one embodiment, the sample from a subject is a fecal specimen or stool. For example, an overgrowth of beta2-toxin-gene-positive *Clostridium perfringens* in the gut includes a range of about $10^3$-$10^4$ CFU per gram dry weight of fecal specimen from a subject. Overgrowth of beta2-toxin-gene-positive *Clostridium perfringens* includes other ranges described herein.

In another embodiment of the invention, the method comprises administering to the subject (e.g., a subject having an overgrowth of beta2-toxin-gene-positive *Clostridium perfringens* in the gut) one or more agents to reduce or eliminate beta2-toxin-gene positive *Clostridium perfringens* in the subject so as to relieve one or more symptoms of autism; thereby treating autism associated with an overgrowth of beta2-toxin-gene-positive *Clostridium perfringens* in the autistic subject.

In another embodiment, the method comprises a) determining an overgrowth of *Clostridium perfringens* positive for beta2-toxin gene in a sample from the subject; and (b) administering to the subject, who has been determined to have the overgrowth of *Clostridium perfringens* positive for beta2-toxin gene in (a), one or more agents to reduce or eliminate beta2-toxin-gene positive *Clostridium perfringens* in the subject so as to relieve one or more symptoms of autism. For example, wherein the sample may be a fecal sample.

In one embodiment of the invention, the overgrowth of beta2-toxin-gene-positive *Clostridium perfringens* is an overrepresentation or excess of beta2-toxin-gene-positive *Clostridium perfringens* vegetative cells, spores or a combination thereof, in the gut of the autistic subject compared to non-autistic subject or population of non-autistic subjects. In one embodiment, overrepresentation of beta2-toxin-gene-positive *Clostridium perfringens* vegetative cells, spores or a combination thereof, may be with respect to total *Clostridium* or total *Clostridium perfringens*. The percent beta2-toxin-gene-positive *Clostridium perfringens* vegetative cells, spores or a combination thereof, as a fraction of total *Clostridium* count or total *Clostridium perfringens* count is higher in the autistic subject compared to non-autistic subject or population of non-autistic subjects.

In one embodiment, the percent beta2-toxin-gene-positive *Clostridium perfringens* vegetative cells, spores or a combination thereof, of total *Clostridium* in the autistic subject is about 3-fold higher than non-autistic subject or population of non-autistic subjects. In one embodiment, the percent beta2-toxin-gene-positive *Clostridium perfringens* vegetative cells, spores or a combination thereof, of total *Clostridium* in the autistic subject is more than 3-fold higher than non-autistic subject or population of non-autistic subjects. In one embodiment, the percent beta2-toxin-gene-positive *Clostridium perfringens* vegetative cells, spores or a combination thereof, of total *Clostridium perfringens* in the autistic subject is more than 3-fold higher than non-autistic subject or population of non-autistic subjects. In one embodiment, the percent beta2-toxin-gene-positive *Clostridium perfringens* vegetative cells, spores or a combination thereof, of total *Clostridium perfringens* in the autistic subject is 10-fold higher than non-autistic subject or population of non-autistic subjects. In one embodiment, the percent beta2-toxin-gene-positive *Clostridium perfringens* vegetative cells, spores or a combination thereof, of total *Clostridium perfringens* in the autistic subject is 20-fold higher than non-autistic subject or population of non-autistic subjects. In one embodiment, the percent beta2-toxin-gene-positive *Clostridium perfringens* vegetative cells, spores or a combination thereof, of total *Clostridium perfringens* in the autistic subject is about 22-fold higher than non-autistic subject or population of non-autistic subjects.

In one embodiment, the amount of beta2-toxin-gene-positive *Clostridium perfringens* vegetative cells, spores or a combination thereof, exceeds mean counts of beta2-toxin-gene-positive *Clostridium perfringens* of a non-autistic subject or population of non-autistic subjects. In one embodiment, the amount of beta2-toxin-gene-positive *Clostridium perfringens* of the autistic subject exceeds $1.48 \times 10^3$ colony forming unit (CFU) per gram dry weight of fecal specimen, the mean counts of beta2-toxin-gene-positive *Clostridium perfringens* of a non-autistic subject or population of non-autistic subjects. In one embodiment, the amount of beta2-toxin-gene-positive *Clostridium perfringens* of the autistic subject is more than $1.48 \times 10^3$ colony forming unit (CFU) per gram dry weight of fecal specimen. In one embodiment, the amount of beta2-toxin-gene-positive *Clostridium perfringens* of the autistic subject exceeds the amount of a non-autistic subject or population of non-autistic subjects by more than 3-fold. In one embodiment, the amount of beta2-toxin-gene-positive *Clostridium perfringens* of the autistic subject exceeds the amount of a non-autistic subject or population of non-autistic subjects by more than 10-fold. In one embodiment, the amount of beta2-toxin-gene-positive *Clostridium perfringens* of the autistic subject exceeds the amount of a non-autistic subject or population of non-autistic subjects by more than 20-fold. In one embodiment, the amount of beta2-toxin-gene-positive *Clostridium perfringens* of the autistic subject exceeds the amount of a non-autistic subject or population of non-autistic subjects by more than 30-fold. In one embodiment, the amount of beta2-toxin-gene-positive *Clostridium perfringens* of the autistic subject exceeds the amount of a non-autistic subject or population of non-autistic subjects by more than 40-fold. In one embodiment, the amount of beta2-toxin-gene-positive *Clostridium perfringens* of the autistic subject exceeds the amount of a non-autistic subject or population of non-autistic subjects by about 44-fold. In one embodiment, the amount of beta2-toxin-gene-positive *Clostridium perfringens* of the autistic subject is more than $4.5 \times 10^3$ colony forming unit (CFU) per gram dry weight of fecal specimen. In one embodiment, the amount of beta2-toxin-gene-positive *Clostridium perfringens* of the autistic subject is more than $1.5 \times 10^4$ colony forming unit (CFU) per gram dry weight of fecal specimen. In one embodiment, the amount of beta2-toxin-gene-positive *Clostridium perfringens* of the autistic subject is more than $3.0 \times 10^4$ colony forming unit (CFU) per gram dry weight of fecal specimen. In one embodiment, the amount of beta2-toxin-gene-positive *Clostridium perfringens* of the autistic subject is more than $4.5 \times 10^4$ colony forming unit (CFU) per gram dry weight of fecal specimen. In one embodiment, the amount of beta2-toxin-gene-positive *Clostridium perfringens* of the autistic subject is more than $6.0 \times 10^4$ colony forming unit (CFU) per gram dry weight of fecal specimen. In one embodiment, the amount of beta2-toxin-gene-positive *Clostridium perfringens* of the autistic subject is about $6.55 \times 10^4$ colony forming unit (CFU) per gram dry weight of fecal specimen.

In another embodiment, the overgrowth of beta2-toxin-gene-positive *Clostridium perfringens* is detected as an overrepresentation or excess of *Clostridium perfringens* vegetative cells, *Clostridium perfringens* spores or combination thereof, in the feces of an autistic subject compared to a control subject or population of control subjects. For example, the control subject or population of control subjects may have about $1.5 \times 10^3$ colony forming units of beta2-toxin-gene-positive *Clostridium perfringens* per gram dry weight of fecal specimen. In another example, the autistic subject has more than about $1.9 \times 10^3$ colony forming units of beta2-toxin-gene-positive *Clostridium perfringens* per gram dry weight of fecal specimen. In yet a further embodiment, the autistic subject may have more than about $6 \times 10^4$ colony forming units of beta2-toxin-gene-positive *Clostridium perfringens* per gram dry weight of fecal specimen.

In one embodiment, overrepresentation of *Clostridium perfringens* vegetative cells, *Clostridium perfringens* spores or combination thereof, is the presence of greater percent *Clostridium perfringens* vegetative cells, *Clostridium perfringens* spores or combination thereof, wherein the percent is determined from the amount of *Clostridium perfringens* vegetative cells, *Clostridium perfringens* spores or combination thereof, in a fecal specimen and dividing by the amount of total *Clostridium* within the same specimen. An overrepresentation of *Clostridium perfringens* vegetative cells, *Clostridium perfringens* spores or combination thereof, for an autistic subject means that the percent *Clostridium perfringens* vegetative cells, *Clostridium perfringens* spores or combination thereof is greater for the autistic subject than in the case of a control subject or a population of control subjects.

In one embodiment, an excess of *Clostridium perfringens* vegetative cells, *Clostridium perfringens* spores or combination thereof, in the feces of an autistic subject means that the number of *Clostridium perfringens* vegetative cells, *Clostridium perfringens* spores or combination thereof, is greater in the case of in the feces of an autistic subject compared to a control subject or population of control subjects.

In one embodiment, the control subject or population of control subjects may be non-autistic subject or population of non-autistic subjects. In one embodiment, the non-autistic subject or population of non-autistic subjects do not have GI symptoms or neurologic disease.

In one embodiment, the autistic subject has GI abnormalities. In one embodiment, the subject may have a different neurologic disease other than autism.

In one embodiment, the autistic subject, control subject or population of control subjects is a child or are children. In one embodiment, the child or children are 3 years of age or younger. In another embodiment, the child or children are less than 12 years of age. In another embodiment, the child or children are less than 14 years of age. In a further embodiment, the child or children are less than 16 years of age. In yet a further embodiment, the child or children are more than 2 years of age. In one embodiment, the child or children are 2-9 years of age. In one embodiment, the child or children is human.

In one embodiment of the invention, the overgrowth of beta2-toxin-gene-positive *Clostridium perfringens* in the gut of an autistic subject may be positively correlated with an overgrowth of *Clostridium perfringens*. For example, the overgrowth of *Clostridium perfringens* may result in at least a 3-fold increase in *Clostridium perfringens* colony forming units in the autistic subject over a control subject or a population of control subjects. In another example, the overgrowth of *Clostridium perfringens* may result in at least a 10-fold increase in *Clostridium perfringens* colony forming units in the autistic subject over a control subject or a population of control subjects.

In yet a further example, the control subject or the population of control subjects may have about $1.7 \times 10^4$ colony forming units of *Clostridium perfringens* per gram dry weight of fecal specimen. In another example, the autistic subject may have more than about $5 \times 10^4$ colony forming units of *Clostridium perfringens* per gram dry weight of fecal specimen. In an additional example, the autistic subject may have more than about $1.7 \times 10^5$ colony forming units of *Clostridium perfringens* per gram dry weight of fecal specimen. In an additional example, the autistic subject may have about $2.1 \times 10^5$ colony forming units of *Clostridium perfringens* per gram dry weight of fecal specimen.

For a value described as being "about" refers to any value within the range of values encompassed by ±10%.

In one embodiment of the invention, the beta2-toxin alters normal cellular process of a host cell afflicted with said toxin, a neighboring cell, or a group of cells participating in communication between the gut and the brain of the subject or a combination thereof. For example, the group of cells may include neurons or nerve cells participating in communication between the gut and the brain of the autistic subject. For example, alteration of normal cellular process may include a genomic effect, a non-genomic effect, a cytotoxic effect or a combination thereof. In an embodiment of the invention, the genomic effect may include a change in gene expression. In yet a further embodiment, the non-genomic effect may include a change in signal transduction, action potential, neurotransmitter release, cell membrane fluidity, cell membrane porosity, cell membrane integrity or a combination thereof. For example, the cytotoxic effect may result in necrosis or apoptosis. In one example, the host cell or the neighboring cell is a cell of the gastrointestinal tract, a neuron innervating the gastrointestinal tract or a combination thereof.

An example of a beta2-toxin-gene-positive *Clostridium perfringens* includes, but is not limited to, a *Clostridium perfringens* beta2-toxin gene, cpb2. In one embodiment, the *Clostridium perfringens* beta2-toxin gene, cpb2, comprises a nucleic acid sequence as given in any of GenBank Accession Nos.: KF155292, GU581185, GU581184, GU581183, GU581182, GU581181, GU581180, GU581179, GU581177, GU581176, HQ853338, HQ853337, HQ853336, HQ853335, HQ853334, HQ853333, HQ853332, HQ853331, HQ853330, HQ853329, AY609177, AY609176, AY609175, AY609174, AY609172, AY609171, AY609170, AY609169, AY609168, AY609167, AY609166, AY609165, AY609163, AY609162, AY609161, GU581178, EU260099, AY730636, AY730635, AY730634, AY730633, AY730632, AY730631, AY730630, EF076030, EF076029, EF076028, AY297455, KJ874348, AY609183, AY609182, AY609181, AY609180, AY609179, AY609178, AY609173, AY609164, AY884041, AY884040, AY884039, AY884038, AY884037, AY884036, AY884035, DQ525205 and L77965.

In one embodiment of the invention, the presence of the *Clostridium perfringens* beta2-toxin gene, cpb2, may be detected with a primer pair direct to sense and anti-sense strands of *Clostridium perfringens* cpb2 gene, having a nucleic acid sequence as given in any of GenBank Accession Nos.: KF155292, GU581185, GU581184, GU581183, GU581182, GU581181, GU581180, GU581179, GU581177, GU581176, HQ853338, HQ853337, HQ853336, HQ853335, HQ853334, HQ853333, HQ853332, HQ853331, HQ853330, HQ853329, AY609177, AY609176, AY609175, AY609174, AY609172, AY609171, AY609170, AY609169, AY609168, AY609167, AY609166, AY609165, AY609163, AY609162, AY609161, GU581178, EU260099, AY730636, AY730635, AY730634, AY730633, AY730632, AY730631, AY730630, EF076030, EF076029, EF076028, AY297455, KJ874348, AY609183, AY609182, AY609181, AY609180, AY609179, AY609178, AY609173, AY609164, AY884041, AY884040, AY884039, AY884038, AY884037, AY884036, AY884035, DQ525205 and L77965. In a particular embodiment, the pair of primers is AGATTTTAAATATGATCCTAACC and CAATACCCTTCACCAAATACTC. In another example, the pair of primers produces a polymerase chain product of 548 bp.

In another embodiment of the invention, the *Clostridium perfringens* beta-toxin gene, cpb, comprises a nucleic acid sequence as given in any of GenBank Accession Nos.: KP064410, KP064409, KP064408, KP064407, KP064406, KP064405, KP064404, GU054492, HQ424445, X83275 and KP768395.

In yet another embodiment, the beta2-toxin-gene-positive *Clostridium perfringens* found in the gut of the subject includes a *Clostridium perfringens* alpha-toxin gene. In another embodiment, the beta2-toxin-gene-positive *Clostridium perfringens* found in the gut of the subject does not include a *Clostridium perfringens* alpha-toxin gene, a *Clostridium perfringens* beta-toxin gene, a *Clostridium perfringens* epsilon-toxin gene, a *Clostridium perfringens* iota-toxin gene or a combination thereof. In yet a further embodiment, the beta2-toxin-gene-positive *Clostridium perfringens* in the gut of an autistic subject comprises a *Clostridium perfringens* alpha-toxin gene but is free of a *Clostridium perfringens* beta-toxin gene, epsilon-toxin gene and iota-toxin gene. In an additional embodiment, the beta2-toxin-gene-positive *Clostridium perfringens* in the gut of an autistic subject is free of a *Clostridium perfringens* alpha-toxin gene, beta-toxin gene, epsilon-toxin gene and iota-toxin gene.

Additionally, in one embodiment of the invention, the beta2-toxin-gene-positive *Clostridium perfringens* produces *Clostridium perfringens* beta2-toxin. In one example, the beta2-toxin-gene-positive *Clostridium perfringens* additionally comprises *Clostridium perfringens* alpha-toxin gene and produces *Clostridium perfringens* beta2-toxin. In another example, the beta2-toxin-gene-positive *Clostridium perfringens* produces *Clostridium perfringens* alpha-toxin. In yet a further example, the beta2-toxin-gene-positive *Clostridium perfringens* produces a toxin that is free of *Clostridium perfringens* alpha-toxin. Additionally, in another example, the beta2-toxin-gene-positive *Clostridium perfringens* is free of *Clostridium perfringens* alpha-toxin, free of a *Clostridium perfringens* beta-toxin, free of a *Clostridium perfringens* epsilon-toxin, free of a *Clostridium perfringens* iota-toxin or a combination thereof. In an additional example, beta2-toxin-gene-positive *Clostridium perfringens* in the gut of an autistic subject produces a *Clostridium perfringens* beta2-toxin and alpha-toxin but is free of a *Clostridium perfringens* beta-toxin, *Clostridium perfringens* epsilon-toxin and *Clostridium perfringens* iota-toxin. In a further example, the beta2-toxin-gene-positive *Clostridium perfringens* in the gut of an autistic subject produces a *Clostridium perfringens* beta2-toxin but is free of a *Clostridium perfringens* alpha-toxin, *Clostridium perfringens* beta-toxin, *Clostridium perfringens* epsilon-toxin and *Clostridium perfringens* iota-toxin. In another example, the beta2-toxin-gene-positive *Clostridium perfringens* in the gut of an autistic subject is free of a *Clostridium perfringens* beta2-toxin, *Clostridium perfringens* alpha-toxin, *Clostridium perfringens* beta-toxin, *Clostridium perfringens* epsilon-toxin and *Clostridium perfringens* iota-toxin. In a further example, the beta2-toxin-gene-positive *Clostridium perfringens* in the gut of an autistic subject produces a toxin other than a *Clostridium perfringens* beta-toxin, *Clostridium perfringens* epsilon-toxin and *Clostridium perfringens* iota-toxin.

In accordance with the practice of the invention, in the composition of the invention, one or more agent(s) includes any of an antimicrobial, a bacteriophage, a probiotic, a probiotic group, a prebiotic or a vaccine which would lead to production of an anti-toxin against a toxin produced by the beta2-toxin-gene-positive *Clostridium perfringens* in the gut of the autistic subject. For example, the agent may be a polypeptide, a nucleic acid or a small molecule which inhibits the transcription of *Clostridium perfringens* beta2-toxin gene, destabilizes a beta2-toxin RNA, inhibits the translation of *Clostridium perfringens* beta2-toxin mRNA transcript, or decreases the half-life of a *Clostridium perfringens* beta2-toxin protein.

Suitable examples of agents to reduce or eliminate beta2-toxin-gene-positive *Clostridium perfringens* include, but are not limited to, ABT-773, ampicillin, sulbactam, amphomycin, azithromycin, bacitracin, carboxmycin, cephlosporins, clarithromycin, erythromycin, furazolidone, nitrofuran, fusidic acid, sodium fusidate, gramicidin, a penem, imipenem, josamycin, linezolid, oxazolidinone, a macrolide, metronidazole, nitroimidazole, mikamycin, minocycline, novobiocin, oleandomycin, triacetyloleandomycin, ostreogrycin, piperacillin, tazobactam, pristinamycin, ramoplanin, ristocetin, rosamicin, rosaramicin, spectinomycin, spiramycin, streptogramin, synergistin, teicoplanin, telithromycin, ticarcillin, clavulanic acid, tyrocidin, tyrothricin, vancomycin, vernamycin, and virginiamycin. Such an agent to reduce or eliminate beta2-toxin-gene-positive *Clostridium perfringens* may be administered singly or in a combination with other agents, concurrently or sequentially, and by any suitable route.

Suitable examples of antimicrobial agents include, but are not limited to, ABT-773, ampicillin, sulbactam, amphomycin, azithromycin, bacitracin, carboxmycin, cephlosporins, clarithromycin, erythromycin, furazolidone, nitrofuran, fusidic acid, sodium fusidate, gramicidin, a penem, imipenem, josamycin, linezolid, oxazolidinone, a macrolide, metronidazole, nitroimidazole, mikamycin, minocycline, novobiocin, oleandomycin, triacetyloleandomycin, ostreogrycin, piperacillin, tazobactam, pristinamycin, ramoplanin, ristocetin, rosamicin, rosaramicin, spectinomycin, spiramycin, streptogramin, synergistin, teicoplanin, telithromycin, ticarcillin, clavulanic acid, tyrocidin, tyrothricin, vancomycin, vernamycin, and virginiamycin. Such an antimicrobial agent may be administered singly or in a combination with other agents, concurrently or sequentially, and by any suitable route.

Suitable examples of a probiotic or the probiotic agent include, but are not limited to, *Bacteroides thetaiotaomicron*, *Bacteroides vulgatus*, *Bacteroides distasonis*, *Bacteroides fragilis*, *Bifidobacterium adolescentis* group, *Eubacterium aerofaciens*, *Clostridium ramosum*, *Escherichia coli*, *Streptococcus faecalis* group, *Lactobacillus* spp., *L. acidophilus*, gram-negative anaerobes, enterococci, *Bacteroides* sp., Parabacteroides, *Prevotella*, *Porphyromonas*, gram-positive anaerobic cocci, *Clostridium* sp., Enterobacteriaceae, *E. coli*, *L. bulgaricus*, *S. thermophilus*, *Collinsella* genus, *Bifidobacterium* genus, *Bifidobacterium longum*, *Bifidobacterium angulatum*, *Dialister invisus*, *Clostridium leptum*, *Firmicutes*, *Actinobacteria*, *Faecalibacterium*, *Ruminococcus*, *Eubacterium*, *Alistipes*, *Roseburia*, *Anaerofilum*, *Streptococcus*, *Turicibacter*, *Parabacteroides*, *Dorea*, *Veillonella*, *Akkermansia*, *Sporobacter*, *Ethanoligenens*, *Papillibacter*, *Holdemania*, *Weissella*, *Dialister*, *Pseudoramibacter*, *Streptococcus*, *Anaerovorax*, *Lactococcus*, *Leuconostoc*, *Ethanoligenens*, *Helcococcus*, *Alkaliphilus*, *Clostridium bolteae*, *Clostridium methylpentosum*, *Eubacterium ruminantium*, *Phascolarctobacterium faecium*, *Alistipes* species, *Bifidobacterium* species, *Lactobacillus* species, and *Bacteroides caccae*. Such a probiotic or the probiotic agent may be administered singly or in a combination with other agents, concurrently or sequentially, and by any suitable route.

Examples of a prebiotic include, but are not limited to, trans-galactooligosaccharide, inulin, Larch arabinogalactan, resistant starch, pectin, beta-glucans, xylooligosaccharides, and a combination thereof. In one embodiment, the prebiotic promotes the growth of gut-colonizing bacteria that compete with the beta2-toxin-gene-positive *Clostridium perfringens* or inhibits the growth of the beta2-toxin-gene-positive *Clostridium perfringens*. In one embodiment, the *Clostridium* sp. is free of beta2-toxin-gene-positive *Clostridium perfringens* of. In one embodiment, the prebiotic promotes the growth of *Bifidobacterium* species, *Lactobacillus* species, Akkermansia, or a combination thereof. A discussion of prebiotics may be found in the following references which are incorporated in their entirety: Gibson G R and Roberfroid M G (1995) J Nutr. 125 (6): 1401-1412; Roberfroid M B (2007) J Nutr. 137 (3 Suppl 2): 830S-7S; Kelly G S (1999) Alternative Medicine Review 4 (2): 96-103; Zaman et al. (2015) Critical Reviews in Biotechnology: 1-7; Gomez et al. (2014) Journal of Agricultural and Food Chemistry 62 (40): 9769-9782; Arena et al. (2014) International Journal of Molecular Sciences 15 (2): 3025-3039; and Jain et al. (2015) Indian Journal of Experimental Biology 53 (3): 131-142.

An example of an anti-toxin agent includes, but is not limited to, an antibody against a toxin.

In one embodiment, the antibody is an antibody against *Clostridium perfringens* beta2-toxin, a fragment of *Clostridium perfringens* beta2-toxin, *Clostridium perfringens* alpha-toxin, a fragment of *Clostridium perfringens* alpha-toxin or a combination thereof. Antibodies *Clostridium perfringens* beta2-toxin are commercially available and well known (J. Zeng et al. Journal of Immunology Research, volume 2016, Article ID 570868; Novus Biologicals). Antibodies *Clostridium perfringens* alpha-toxin are commercially available and well known (H. Saito, et al., FEMS Microbiology Letters (1989), 59:173-176; US Biological).

In another embodiment, the antibody is an antibody against a toxin from a beta2-toxin-gene-positive *Clostridium perfringens* wherein the toxin is not *Clostridium perfringens* beta2-toxin or its fragment, *Clostridium perfringens* alpha-toxin or its fragment, *Clostridium perfringens* beta-toxin or its fragment, *Clostridium perfringens* epsilon-toxin or its fragment, or *Clostridium perfringens* iota-toxin or its fragment.

For example, the antibody may be a neutralizing antibody or an inhibitory antibody.

In one embodiment, the antibody is a polyclonal antibody, a monoclonal antibody, an antigen-binding fragment of an antibody or a bispecific antibody.

In a further embodiment, the antigen-binding fragment of an antibody comprises a Fab antibody fragment, a $F(ab')_2$ antibody fragment, a Fv antibody fragment or a single chain variable fragment (scFv).

Suitable examples of toxins include, but are not limited to, *Clostridium perfringens* beta2-toxin and *Clostridium perfringens* alpha-toxin.

In one embodiment, the vaccine comprises *Clostridium perfringens* beta2-toxin, a fragment of *Clostridium perfringens* beta2-toxin, *Clostridium perfringens* alpha-toxin, a fragment of *Clostridium perfringens* alpha-toxin or a combination thereof.

In another embodiment, the vaccine is free of *Clostridium perfringens* beta-toxin, a fragment of *Clostridium perfringens* beta-toxin, *Clostridium perfringens* epsilon-toxin, a fragment of *Clostridium perfringens* epsilon-toxin, *Clostridium perfringens* iota-toxin, a fragment of *Clostridium perfringens* iota-toxin or a combination thereof.

In another embodiment, the vaccine comprises a toxin or a fragment thereof produced by the beta2-toxin-gene-positive *Clostridium perfringens* wherein the toxin is not *Clostridium perfringens* beta2-toxin or its fragment, *Clostridium perfringens* alpha-toxin or its fragment, *Clostridium perfringens* beta-toxin or its fragment, *Clostridium perfringens* epsilon-toxin or its fragment, or *Clostridium perfringens* iota-toxin or its fragment.

A suitable example of a vaccine is one that leads to the production of an antibody against *Clostridium perfringens* beta2-toxin or *Clostridium perfringens* alpha-toxin or a combination thereof. For example, the antibody may be free of an antibody against *Clostridium perfringens* beta-toxin, *Clostridium perfringens* epsilon-toxin or *Clostridium perfringens* iota-toxin or a combination thereof. In a separate embodiment, the vaccine leads to the production of an antibody against a toxin produced by the beta2-toxin-gene-positive *Clostridium perfringens* wherein the toxin is not *Clostridium perfringens* beta2-toxin, *Clostridium perfringens* alpha-toxin, *Clostridium perfringens* beta-toxin, *Clostridium perfringens* epsilon-toxin or *Clostridium perfringens* iota-toxin.

Suitable examples of agents that reduce or eliminate beta2-toxin-gene-positive *Clostridium perfringens* include, but are not limited to, an antibody, a lectin, a protease, or a protein, peptide, carbohydrate or small molecule that interacts with beta2-toxin of *Clostridium perfringens*. In one embodiment, the antibody is an anti-beta2-toxin antibody. In another embodiment, the antibody inhibits activity, decreases stability or alters localization of beta2-toxin of *Clostridium perfringens*. Additionally, examples of a protein, peptide, carbohydrate or small molecule that interact with beta2-toxin are those that inhibit formation of a functional toxin, prevent post-translational modification, prevent protein assembly, prevent formation of a potential pore-forming complex, prevent association with chaperone protein, accessory protein or receptor, promote degradation of said toxin, mis-localize said beta2-toxin, inhibit expression of said beta2-toxin or stabilize beta2-toxin with a natural inhibitor to *Clostridium perfringens* beta2-toxin so as to maintain an inactive state of the *Clostridium perfringens* beta2-toxin. Merely by way of example, the natural inhibitor may be an inhibitor to *Clostridium perfringens* beta2-toxin present in fecal material or sample. In another example, the protein, peptide, carbohydrate or small molecule are those that prevent normal folding or assembly of the beta2-toxin, prevent insertion of the beta2-toxin into a cell membrane, prevent interaction with other toxin subunits and prevent its function as a pore-forming toxin.

In one embodiment, an agent that reduces or eliminates beta2-toxin-gene-positive *Clostridium perfringens* may be a bacteriophage. The bacteriophage may be virulent for *Clostridium perfringens*. In one embodiment, examples of bacteriophages virulent for *Clostridium perfringens* include, but are not limited to, bacteriophages from the Siphoviridae family and Podoviridae family. Suitable members of the Siphoviridae family virulent for *Clostridium perfringens* and may be used in a bacteriophage or phage therapy to reduce or eliminate beta2-toxin-gene-positive *Clostridium perfringens* or beta-toxin-gene-related toxin-gene-positive *Clostridium perfringens* include ΦCP39O and ΦCP26F (Seal et al., Arch. Virol. 2011; 156:25-35 [PubMed: 20963614]). Suitable members of the Podoviridae family virulent for *Clostridium perfringens* and may be used in a bacteriophage or phage therapy to reduce or eliminate beta2-toxin-gene-positive *Clostridium perfringens* include ΦCPV1 (Volozhantsev et al., Virus Res. 2011; 155:433-439 [PubMed: 21144870]), ΦCP24R (Morales et al., Arch. Virol. 2012; 157:769-772 [PubMed: 22218967]), ΦCPV4, ΦZP2, and ΦCP7R (Volozhantsev et al., PLoS ONE. 2012; 7:e38283 [PubMed: 22666499]. Use of bacteriophages virulent for *Clostridium perfringens* and its gene products to control animal and human diseases without having deleterious effects on beneficial probiotic bacteria are discussed in Seal et al., Poult Sci. 2013; 92(2): 526-533, whose reference is incorporated in its entirety. An agent to reduce or eliminate beta2-toxin-gene-positive *Clostridium perfringens* may be administered singly or in a combination with other agents, concurrently or sequentially, and by any suitable route.

The invention further provides methods of identifying an autistic subject whose autism may be alleviated by a course of treatment directed against an overgrowth of beta2-toxin-positive *Clostridium perfringens* so as to reduce or eliminate the overgrowth. In one embodiment, the method comprises (a) determining existence of said overgrowth in the autistic subject, thereby identifying the autistic subject whose autism may be alleviated by a course of treatment directed against the overgrowth of beta2-toxin-positive *Clostridium perfringens*.

In another embodiment, the overgrowth of *Clostridium perfringens* comprises an overgrowth of beta2-toxin-positive *Clostridium perfringens*.

In another further embodiment, the overgrowth of *Clostridium perfringens* is an overgrowth of beta2-toxin-positive *Clostridium perfringens*.

In one embodiment, the step of determining the existence of said overgrowth in the autistic subject comprises (a) detecting presence of beta2-toxin-positive *Clostridium perfringens* in a sample from the subject; (b) quantifying the amount of beta2-toxin-positive *Clostridium perfringens* in the sample; (c) comparing the value in (b) with a value for the amount of beta2-toxin-positive *Clostridium perfringens* in non-autistic subject or subjects; and (d) finding that the value of (b) is greater than the value from non-autistic subject or subjects. In one embodiment, the value of (b) being greater than the value from non-autistic subject or subjects is a statistically significant difference. The *Clostridium perfringens* may include a vegetative cell, spore or combination thereof.

In another embodiment of the invention, the method comprises (a) determining existence of said overgrowth in the autistic subject, thereby identifying the autistic subject whose autism may be alleviated by a course of treatment directed against the overgrowth of beta2-toxin-producing *Clostridium perfringens*. Further, in one embodiment, the step of determining existence of said overgrowth in the autistic subject comprises (a) detecting presence of beta2-toxin-positive *Clostridium perfringens* in a sample from the subject; (b) quantifying the activity of *Clostridium perfringens* beta2-toxin in a sample from the subject; (c) comparing the value in (b) with a value for the activity of *Clostridium perfringens* beta2-toxin in a sample or samples from non-autistic subject or subjects; and (d) finding that the value of (b) is greater than the value of sample or samples from non-autistic subject or subjects.

In yet a further embodiment, the method comprises the step of determining the presence of said beta2-toxin in the autistic subject, thereby, identifying the autistic subject whose autism may be alleviated by a course of treatment directed against beta2-toxin of *Clostridium perfringens*. The method further comprises (b) quantifying activity of beta2-toxin; (c) comparing a value obtained in (b) against a threshold value; and (d) finding greater activity of beta2-toxin in the autistic subject. In one embodiment, the *Clostridium perfringens* comprises a vegetative cell. In an embodiment of the invention, the fecal material of the autistic subject is used to determine said overgrowth. In yet another embodiment, the fecal material of the autistic subject is used to determine presence of beta2-toxin of *Clostridium perfringens*. In an additional embodiment, the presence of beta2-toxin of *Clostridium perfringens* is determined by detecting the presence of nucleic acid encoding beta2-toxin of *Clostridium perfringens* or presence of polypeptide for beta2-toxin of *Clostridium perfringens*. In an additional embodiment, the presence of beta2-toxin of *Clostridium perfringens* is determined by determining the activity of beta2-toxin of *Clostridium perfringens*.

The invention further provides methods of screening autistic subjects whose autism may be alleviated by a course of treatment directed against beta2-toxin of *Clostridium perfringens* by identifying the subject by any of the methods of the invention.

The invention additionally provides methods for monitoring the course of autism in an autistic subject by identifying the subject by any of the methods of the invention and quantitatively determining a level of overgrowth of *Clostridium perfringens*, overgrowth of beta2-toxin-gene-positive *Clostridium perfringens*, activity of *Clostridium perfringens* beta2-toxin from a biological sample from the subject at one time point and comparing a value so determined with the value determined from in a second sample from the subject, such samples being taken at different points in time, a difference in the values determined being indicative of the course of the autistic condition.

In one embodiment, a decrease in the overgrowth of *Clostridium perfringens*, overgrowth of beta2-toxin-gene-positive *Clostridium perfringens*, activity of *Clostridium perfringens* beta2-toxin is indicative or predictive of reducing severity or duration of one or more symptoms associated with autism.

In another embodiment, an increase in the overgrowth of *Clostridium perfringens*, overgrowth of beta2-toxin-gene-positive *Clostridium perfringens*, activity of *Clostridium perfringens* beta2-toxin is indicative or predictive of reducing severity or duration of one or more symptoms associated with autism.

In another embodiment, one or more symptoms associated with autism is any of early onset autism, late stage autism or regressive autism.

In a further embodiment, a method of treating autism associated with an overgrowth of beta2-toxin-gene-positive *Clostridium perfringens* in the gut of an autistic subject comprising: a) determining existence of an overgrowth of *Clostridium perfringens* positive for beta2-toxin gene in a sample from the subject; and (b) administering to the subject one or more agents to reduce or eliminate beta2-toxin-gene positive *Clostridium perfringens* in the subject so as to relieve one or more symptoms of autism; thereby, treating autism associated with an overgrowth of beta2-toxin-gene-positive *Clostridium perfringens* in the autistic subject. In one embodiment, an antimicrobial used to treat autism associated with an overgrowth of beta2-toxin-gene-positive *Clostridium perfringens* so as to reduce or eliminate beta2-toxin-gene-positive *Clostridium perfringens* should have certain characteristics for optimal benefit and minimal side effects. Certain antimicrobials have characteristics appropriate to treat even very young children, and such drugs are useful to treat disorders having the gut-brain involvement. Preferably, an antimicrobial selected as a therapy will have one or more of the following properties:

1) Good in vitro activity against beta2-toxin-gene-positive *Clostridium perfringens*;
2) Relatively poor activity against most other organisms normally found in the gut flora;
3) Safe doses capable of achieving a concentration in the colon or elsewhere in the GI tract where the offending organism proliferates exceeding the minimal inhibitory concentration or minimal bactericidal concentration of the drug by at least four or five-fold concentrations;
4) Preferably absorbed very little or not at all when given orally (to minimize systemic effects);

5) Bactericidal activity preferred (rather than purely inhibitory activity);
6) Not cross-resistant with vancomycin or other drugs that are important for treatment of systemic infections;
7) Resistance does not develop readily (i.e., the drug does not readily engender resistance in bacteria);
8) Palatable in liquid form when taken orally (for administration to children), or readily formulated into other oral doses (to enhance patient compliance);
9) Well tolerated orally over extended period of time (preferably at least 3-4 months);
10) Little or no toxicity, either systemically or in the bowel;
11) Preferably effective when given only once or twice daily; and
12) Preferably moderate in price.

Drugs that have one or more of the above characteristics may have utility for antimicrobial therapy in treating neurological disorders with gut flora etiology, such as those associated with an overgrowth of beta2-toxin-gene-positive *Clostridium perfringens*.

Appropriate doses of the antimicrobials (as given above) are within the range given for many other conditions for which the antimicrobials are prescribed. Dosage information can be found, for example, in the Physicians' Desk Reference, 54$^{th}$ edition, Medical Economics Company, Montvale, N.J. (2000 or subsequent editions). In certain instances, the doses may be elevated to the extent necessary to maintain a bactericidal or bacteriostatic concentration throughout the gastrointestinal tract. The antimicrobials are preferably formulated for oral administration, such as in liquid form, tablet, capsule, granules, chewable, etc. Tablets or capsules may be enterically coated to minimize gastric absorption of the drug when the pH of the stomach is high or emptying is slow due to certain drugs or diseases, the stomach can be colonized with many bacteria.

The antimicrobials can be administered as known in the art. It is desirable to select a route of administration that is most effective for the therapy, examples thereof being oral administration or parenteral administration such as intravenous administration with subsequent excretion into the bowel.

A preferred compound for treating *Clostridium* overgrowth in the gut is ramoplanin, also known as A-16686 (see, e.g., U.S. Pat. Nos. 4,303,646; 4,328,316; 4,427,656; 5,539,087; and 5,925,550; and Parenti et al.; *Drugs Exp Clin Res* 16(9):451-5 (1990); all herein incorporated by reference). This antibiotic is not cross-resistant with vancomycin, it engenders very little to no resistance in bacteria, is not detectably absorbed systemically in humans (making it exceptionally safe, even for young children), can be made palatable in a liquid form, achieves high concentrations in the large intestine, has very good activity against clostridia, can be given twice a day, and is primarily active against gram positive organisms at the dosage levels administered. Ramoplanin is preferable to drugs such as vancomycin and metronidazole, which have previously been used, because, for example, vancomycin, while achieving a high concentration in the intestines throughout, is effective against *Bacteroides*, a beneficial genus of gut flora, as well as clostridial species. In a special formulation it is also a potent antibiotic against, e.g., systemic methicillin-resistant *Staphylococcus* infections, and widespread use for other purposes risks inducing vancomycin-resistant *Staphylococcus* or other species. Metronidazole, on the other hand, is not an ideal candidate because of its ready systemic absorption, which can lead to neurotoxic side effects when given in high enough concentrations to remain effective in the gut, and the fact that it is quite bitter and thus difficult to formulate as a liquid for oral use.

When using antimicrobial in treating autism associated with an overgrowth of beta2-toxin-gene-positive *Clostridium perfringens*, it is desirable to minimize the extent of normal bacterial flora disruption of the gut during antimicrobial treatment. As such, it is highly desirable to tailor an antimicrobial therapy as specifically as possible against beta2-toxin-gene-positive *Clostridium perfringens*.

When using a probiotic or probiotic agent to treat autism associated with an overgrowth of beta2-toxin-gene-positive *Clostridium perfringens*, dosage (colony forming units (cfu) of each bacterium) is preferably at least the number found in the mean count/gram, and is supplied to the patient daily or twice daily for a number of days until it is determined that the bacteria have become established. The formulation can be provided as active cells or spores. It can be provided in an enterically coated form (e.g., for active cells) to protect sensitive cells from the gastric environment. A preferred therapy involves temporary elimination or suppression of the patient's flora (primarily or entirely with the use of antimicrobial agents, preferably directed specifically against beta2-toxin-gene-positive *Clostridium perfringens*) and introduction of a new, non-pathogenic flora that consists of a number of bacteria normally found in the bowel that convey colonization resistance (to prevent regrowth or reimplantation of the offending bacteria). Therapies are preferably patterned after those described in the poultry literature, for example, Wooley et al., *Avian Dis.* 43(2):245-50, (1999); Hume et al., *J. Food Prot.* 61(6):673-6 (1998); Corrier et al., *J. Food Prot.* 61(7):796-801 (1998); Hume et al., *Avian Dis.* 40(2):391-7 (1996); Corrier et al., *Poult Sci.* 74(7):1093-101 (1995); and Corrier et al., *Poult Sci.* 74(6): 916-24 (1995), all herein incorporated by reference.

Alternatively, bacteriophage specific for the bacterium producing the toxin can be introduced to the patient's gastrointestinal tract to reduce or kill the toxin-producing bacteria, and probiotic therapy mixtures can be concurrently or subsequently administered. An example of a successful protocol involving this strategy with *Clostridium difficile* can be found in Ramesh et al., *Anaerobe* 5:69-78 (1999), herein incorporated by reference. Bacteriophage may be susceptible to gastric acidity and such acidity should be neutralized prior to phage administration, or else the bacteriophage can be administered in an enterically coated tablet or capsule.

Probiotic therapy can be used in conjunction with antimicrobials used to treat infections in otherwise normal patients (i.e., before the onset of aneurological disorder) in order to prevent or reduce the risk of the occurrence of a neurological disorder. Alternatively, it can be used in conjunction with antimicrobials being used to reduce, eliminate or inhibit the beta2-toxin-gene-positive *Clostridium perfringens* species overgrown in a patient's gastrointestinal tract, and to promote the re-emergence of normal gut flora. In one embodiment, probiotic therapy may take the form of a fecal therapy using fecal material obtained from a normal subject without autism or GI abnormality and this fecal material is administered to an autistic subject with an overgrowth of beta2-toxin-gene-positive *Clostridium perfringens* alone or in combination with an antimicrobial, a different probiotic, a different probiotic group, a prebiotic, a bacteriophage or a vaccine.

The following Examples are intended to be illustrative rather than encompassing.

EXAMPLES

Example 1

Figure 1:
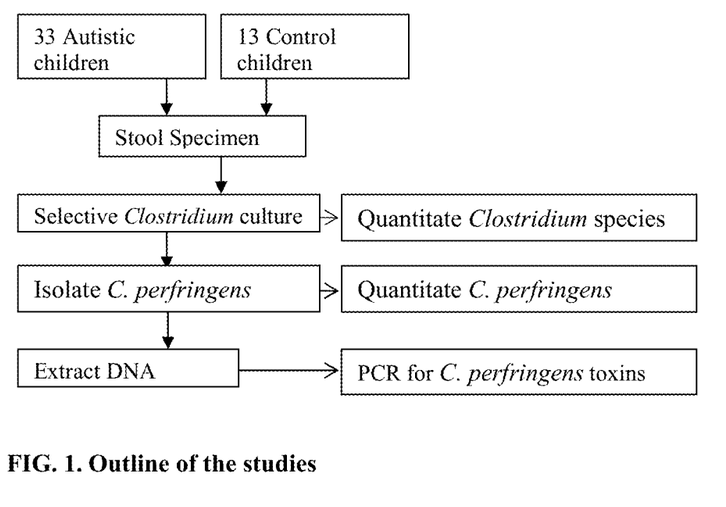
FIG. 1 indicates an outline of an analysis of stool specimens from autistic children and control children.
Figure 2:
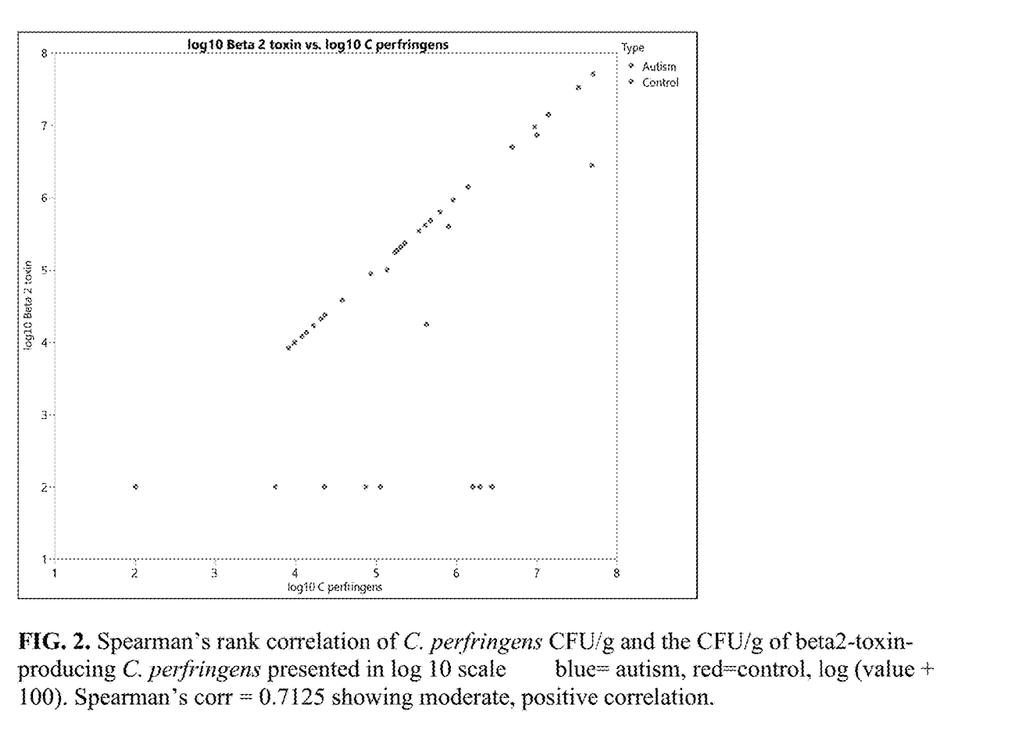
FIG. 2 is a diagram illustrating correlation between *C. perfringens* CFU/g and the CFU/g of beta2-toxin-producing *C. perfringens* presented in log 10 scale.
Figure 3:
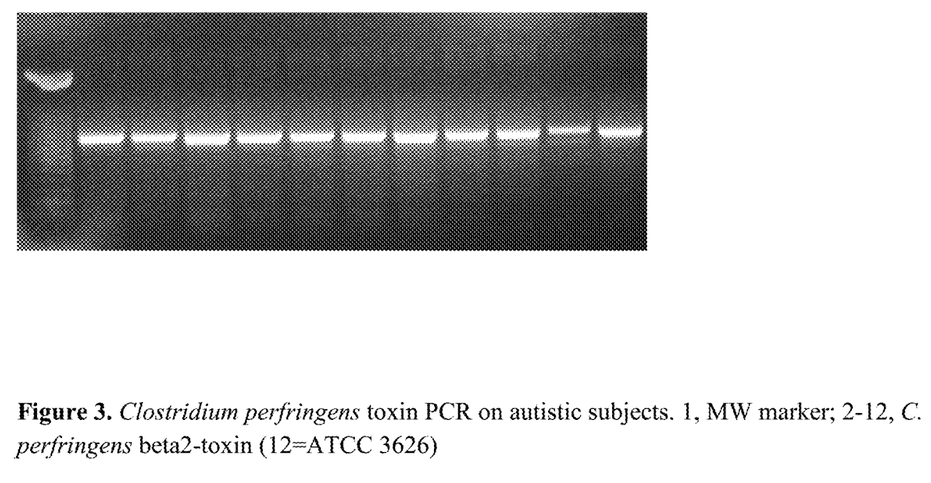
FIG. 3 is a PCR analysis of toxin genes of *Clostridium perfringens*.

We studied stool specimens from 33 autistic children aged 2-9 years with GI abnormalities and 13 control children without autism and without GI symptoms (FIG. 1). We performed quantitative comparison of overall *Clostridium* species, *C. perfringens* strains from the fecal microflora of autistic and control children by conventional, selective anaerobic culture methods. We performed PCR analysis for main *C. perfringens* toxins.

Materials and Methods

*Clostridium* Culture.

This study used previously processed and homogenized stool specimens stored frozen at −80° C. Aliquots of the homogenized specimens were diluted 1:10 in pre-reduced thioglycollate broth (Anaerobe Systems, Morgan Hill, Calif.). For the selective isolation of *Clostridium*, these diluted aliquots of the stool specimens were processed two ways, utilizing ethanol and heat treatments, to select spores. For ethanol treatment, a 1 ml aliquot was incubated with 100% ethanol for 10 minutes. For heat treatment, the rest of the thioglycollate tube was incubated at 80° C. for 10 min. Subsequently, 10-fold serial dilutions were plated (100 µl/plate) onto *Brucella* and CDC agar plates (Anaerobe Systems) from both preparations. The plates were incubated under anaerobic conditions at 37° C. for 72 h before initial inspection and re-incubated up to 7 days (8). Anaerobic conditions consisted of a gas mixture of 5% $CO_2$, 5% $H_2$, and 90% $N_2$; the residual oxygen was removed by palladium catalysts. *Clostridium* colonies were counted and the counts were adjusted to dry weight of stool. Similarly, characteristic *C. perfringens* colony types were counted and the counts were adjusted to dry weight of stool. Single *C. perfringens* colonies were selected, described and subcultured on *Brucella* agar and incubated for 48 h., as described above. Additionally, as a back-up enrichment culture, the heat-treated thioglycollate tubes were incubated at 37° C. for 72 h and then let stand at room temperature for one week before subculturing.

Reference Strains.

*C. perfringens* reference strains ATCC 3626 and ATCC 14809 were obtained from the American Type Culture Collection (ATCC). The strains were grown 48 h on *Brucella* agar and processed as described below.

DNA Extraction.

For PCR analysis of *C. perfringens*, several single colonies obtained after 48 h cultivation on *Brucella* agar were inoculated into 250 µl nuclease-free water and boiled for 20 min to lyse the cells. After centrifugation at 13000 g for 5 min at room temperature, the supernatant fluid was removed and used in the PCR reaction.

Toxin PCR.

PCR assay to detect the genes for *C. perfringens* a-toxin (cpa), b-toxin (cpb), b2-toxin (cpb2), i-toxin (iA), and enterotoxin (cpe) was performed using primer pairs as shown in Table 1. The *C. perfringens* strains were typed utilizing methods as previously described (9, 10) with the exception that instead of multiplex PCR, single PCR's were performed with each primer pair. The PCR conditions were as follows: DNA was denatured for 2 min at 95° C. and amplified for 35 cycles (1 min at 94° C., 1 min at 55° C., 1 min at 72° C. for denaturation, annealing and extension phases, respectively), followed by an additional period of extension for 10 min at 72° C. PCR products were separated by electrophoresis in a 2% (w/v) agarose gel stained with ethidium bromide. Amplified bands were visualized and photographed under UV illumination.

Verification of PCR Products.

Verification of the PCR products was done by DNA sequencing of purified PCR product. The PCR products were excised from an agarose gel and purified using the QIAquick gel extraction kit (Qiagen, Valencia, Calif.). The purified PCR products were sequenced directly with a Biotech Diagnostic Big Dye sequencing kit (Biotech Diagnostics, CA) on an ABI 3130 Avant sequencer (Applied Biosystems, Foster City, Calif.). The sequencing data were analyzed by comparison of the consensus sequences with GenBank sequences by using Ribosomal Database Project (RDP-II) (Michigan State University, East Lansing) (11), and Basic Local Alignment Search Tool (BLAST) (12). Analyses of the sequences were performed by comparing with the sequences of the type strains retrieved from GenBank by using the program Clustal W (13).

Results

We performed quantitative, selective anaerobic culture from stool specimens of 33 autistic children and 13 control children (7) (Table 2). Overall, the mean colony-forming unit (CFU) *Clostridium* cell count obtained from stool samples of the autistic children was $9.2\times10^7$ cfu/g dry weight, and $4.73\times10^7$ cfu/g dry weight from normal control children. 30/33 and 10/13 autism and control samples, respectively, yielded *C. perfringens*. The mean colony forming unit (CFU) *C. perfringens* cell count obtained from stool samples of the autistic children was $2.12\times10^5$ cfu/g dry weight, and $1.7\times10^4$ cfu/g dry weight from normal control children. Altogether, we isolated 111 different *C. perfringens* strains (based on colony morphology) from the autism samples and 23 from the control samples. The PCR analysis (8) for clostridial toxins of these *C. perfringens* isolates (FIG. 3) revealed that autism samples had statistically significantly ($p=0.014$) higher incidence of *C. perfringens* beta2-toxin (Table 2). The mean CFU of beta2-toxin-producing *C. perfringens* cell count obtained from stool samples of the autistic children was $6.55\times10^4$ cfu/g dry weight, and $1.48\times10^3$ cfu/g dry weight from normal control children. *C. perfringens* CFU/g and the CFU/g of beta2-toxin-producing *C. perfringens* were moderately, positively correlated (Spearman corr=0.7125) (FIG. 2).

Discussion

*C. perfringens* beta2-toxin was first studied and described in 1997 by Popoff's group (5). Initially it was found in enteric disease in animals (piglets, horses) and in food. Subsequently, it was found in other animals and in soil, and finally in humans. *C. perfringens* isolates carrying beta2-toxin have been described in human gastrointestinal diseases, including food poisoning, antibiotic-associated diarrhea (AAD) and sporadic diarrhea (SD). Altogether, 24% (7/29) isolates from humans with food poisoning were shown to produce beta2-toxin; whereas, 76% (34/46) isolates from humans suffering with either AAD or SD were beta2-toxin positive (15). Thirty-four of these AAD- and SD-isolates produced beta2-toxin in vitro, whereas only one food poisoning isolate produced the toxin in vitro. From the one healthy person tested, a beta2-toxin-harboring *C. perfringens* was also isolated and was capable of producing the beta2-toxin in vitro (15). Another study characterizing *C. perfringens* isolates of SD patients demonstrated the presence of beta2-toxin in 87% (12/14) isolates; ten of these isolates produced the beta2-toxin in vitro (16). In a study of fecal samples of 43 healthy North Americans, 13 (30%) people had beta2-toxin-harboring *C. perfringens* (17).

Our findings suggest that the involvement of beta2-toxin in autism is remarkable, with 79% of the 33 autism patients showing its presence in feces, compared to 38% of the 13 control subjects. Our results are similar to reports where subjects with AAD and SD were shown to harbor 76-87% of beta2-toxin producing *C. perfringens* (15, 16), and normal healthy subjects 30% (17).

We have not seen this high incidence with any of the other bacteria that we have described as having involvement in autism.

3. Finegold S M. Therapy and epidemiology of autism—clostridial spores as key elements. Medical hypotheses 2008; 70:508-511.
4. Song Y, Liu C, Finegold S. M. Real-time PCR quantitation of clostridia in feces of autistic children. Appl Environ Microbiol 2004; 70:6459-6465.
5. Popoff M R, Poulain B. Bacterial toxins and the nervous system: neurotoxins and multipotential toxins interacting with neuronal cells. Toxins 2010; 2:683-737.
6. Gibert M, Jolivet-Reynaud C, Popoff M R. Beta2 toxin, a novel toxin produced by *Clostridium perfringens*. Gene. 1997 Dec. 5; 203(1):65-73.

TABLE 1

Primers for PCR detection of *Clostridium perfringens* toxin genes cpa, cpb, cpb2, etx, iA and cpe

| | Forward primer | Reverse primer | Size | Ref |
|---|---|---|---|---|
| cpa | GCTAATGTTACTGCCGTTGA | CCTCTGATACATCGTGTAAG | 324 | 9 |
| cpb | GCGAATATGCTGAATCATCTA | GCAGGAACATTAGTATATCTTC | 196 | 9 |
| cpb2 | AGATTTTAAATATGATCCTAACC | CAATACCCTTCACCAAATACTC | 548 | 10 |
| cpe | GGAGATGGTTGGATATTAGG | GGACCAGCAGTTGTAGATA | 233 | 9 |
| cpetx | TGGGAACTTCGATACAAGCA | AACTGCACTATAATTTCCTTTTC C | 655 | 9 |
| cpia | ACTACTCTCAGACAAGACAG | CTTTCCTTCTATTACTATACG | 446 | 9 |

TABLE 2

*Clostridium perfringens* mean counts (CFU/g) and toxin typing of isolates from fecal specimens of autistic and control children

| | Specimens | | CFU/g | | | Number of positive specimens | | | | | |
|---|---|---|---|---|---|---|---|---|---|---|---|
| | Total | *C. perfringens* isolated | *Clostridium* | *C. perfringens* | Beta2-Toxin-positive *C. perfringens* | Beta2-Toxin | CPE | Alpha | Beta | Epsilon | Iota |
| Autism | 33 | 30 | 9.20E+07 | 2.12E+05 | 6.55E+04 | 26/33 (79%) | 3/33 (9%) | 30 | 0 | 0 | 0 |
| Control | 13 | 10 | 4.73E+07 | 1.70E+04 | 1.48E+03 | 5/13 (38%) | 1/13 (8%) | 10 | 0 | 0 | 0 |
| p-value | | | 0.17^ | 0.031^ | 0.0028^ 0.015^^ | 0.014* | | | | | |

^t-test;
^^Wilcoxon t-test
*2-tail Fisher exact test

REFERENCES

1. Sandler R H, Finegold S M, Bolte E R, Buchanan C P, Maxwell A P, Vaisanen M L, Nelson M N, Wexler H M. Short-term benefit from oral vancomycin treatment of regressive-onset autism. J Child Neurol 2000; 15:429-435.
2. Finegold S M, Molitoris D, Song Y, Liu C, Vaisanen M-L, Bolte E, McTeague M, Sandler R, Wexler H, Marlowe E M, Collins M D, Lawson P A, Summanen P, Baysallar M, Tomzynski T J, Read E, Johnson E, Rolfe R, Nasir P, Shah H, Haake D A, Manning P, Kaul A. Gastrointestinal microflora studies in late-onset autism. Clin Infect Dis 2002; 35 (Suppl.1):S6-S16.
7. Fisher D J. *Clostridium perfringens* beta2 toxin: a potential accessory toxin in gastrointestinal diseases of humans and domestic animals. Theses. 2006. University of Pittsburgh.
8. Jousimies-Somer H R, Summanen P, Citron D, Baron E, Wexler H M, Finegold S. M. Wadsworth-KTL Anaerobic Bacteriology Manual, 6$^{th}$ Edit, Belmont, C A: Star Publishing, 2002.
9. Meer R R, Songer J G. Multiplex polymerase chain reaction assay for genotyping *Clostridium perfringens*. Am J Vet Res. 1997 July; 58(7):702-5.
10. Garmory H S, Chanter N, French N P, Bueschel D, Songer J G, Titball R W. Occurrence of *Clostridium perfringens* b2-toxin amongst animals, determined using genotyping and subtyping PCR assays. Epidemiol. Infect. 2000; 124, 61-67.

11. Maidak B L, Cole J R, Lilburn T G, Parker C T, Saxman P R, Farris R J, Garrity G M, Olsen G J, Schmidt T M, Tiedje J M. The RDP-II (Ribosomal Database Project). Nucleic Acid Res 2001; 29:173-174.
12. Benson D A, Kars I, Lipman D J, Ostell J, Rapp B A, Wheeler D L. GenBank. Nucleic Acid Res 2002; 30:17-20.
13. Higgins D, Thompson J, Gibson T, Thompson J D, Higgins D G, Gibson T J. CLUSTAL W: improving the sensitivity of progressive multiple sequence alignment through sequence weighting, position-specific gap penalties and weigh matrix choice. Nucleic Acid Res 1994; 22:4673-4680.
14. Rumah K R, Linden J, Fischetti V A, Vartanian T. (2013). Isolation of *Clostridium perfringens* Type B in an Individual at First Clinical Presentation of Multiple Sclerosis Provides Clues for Environmental Triggers of the Disease. Plos One, 8, e76359.
15. Fisher D J, Miyamoto K, Harrison B, Akimoto S, Sarker M R, McCLane B A. Association of beta2 toxin production with *Clostridium perfringens* type A human gastrointestinal disease isolates carrying a plasmid enterotoxin gene. Molecular Microbiology 2005; 56:747-762.
16. Harrison B, Raju D, Garmory H S, Brett M M, Titball R W, Sarker M R. Molecular characterization of *Clostridium perfringens* isolates from humans with sporadic diarrhea: evidence for transcriptional regulation of the beta2-toxin-encoding gene. Applied and Environmental Microbiology 2005; 71: 8362-8370.
17. Carman, R. J., Sayeed, S., Li, J., Genheimer, C. W., Hilton-Smith, M. F., Wikins, T. D., McClane, B. A., 2008. *Clostridium perfringens* toxin genotypes in the feces of healthy North Americans. Anaerobe 2008; 14:102-108.

What is claimed is:

1. A method of reducing levels of beta2-toxin *Clostridium perfringens* in the gut of an autistic subject, the method comprising administering to the autistic subject an anti-toxin of a *Clostridium perfringens* beta2-toxin gene in an amount effective to reduce the *Clostridium perfringens* beta2-toxin gene in the gut of the autistic subject, wherein a fecal sample of the autistic subject prior to administration has more than about $1.5 \times 10^3$ colony forming units of beta2-toxin-gene-positive *Clostridium perfringens* per gram dry weight of fecal specimen, and wherein a fecal sample of the autistic subject subsequent to administration has less colony forming units of beta2-toxin-gene-positive *Clostridium perfringens* per gram dry weight of fecal specimen than the fecal sample prior to administration.

2. The method of claim 1, wherein a fecal sample of the autistic subject prior to administration has beta2-toxin-gene-positive *Clostridium perfringens* present in an amount that is greater than the amount of beta2-toxin-gene-positive *Clostridium perfringens* present in a fecal specimen of a control subject.

3. The method of claim 1, wherein a fecal specimen of the autistic subject prior to administration has beta2-toxin-gene-positive *Clostridium perfringens* present in an amount that is at least about 3-fold higher than the amount of beta2-toxin-gene-positive *Clostridium perfringens* present in a fecal specimen of a control subject.

4. The method of claim 1, wherein a fecal specimen of the autistic subject prior to administration comprises *Clostridium perfringens* that comprises a *Clostridium perfringens* alpha-toxin gene.

SEQUENCE LISTING

```
<160> NUMBER OF SEQ ID NOS: 2

<210> SEQ ID NO 1
<211> LENGTH: 23
<212> TYPE: PRT
<213> ORGANISM: Artificial Sequence
<220> FEATURE:
<223> OTHER INFORMATION: Synthetic Construct

<400> SEQUENCE: 1

Ala Gly Ala Thr Thr Thr Thr Ala Ala Ala Thr Ala Thr Gly Ala Thr
1               5                   10                  15

Cys Cys Thr Ala Ala Cys Cys
            20

<210> SEQ ID NO 2
<211> LENGTH: 22
<212> TYPE: PRT
<213> ORGANISM: Artificial Construct
<220> FEATURE:
<223> OTHER INFORMATION: Synthetic Construct

<400> SEQUENCE: 2

Cys Ala Ala Thr Ala Cys Cys Cys Thr Thr Cys Ala Cys Cys Ala Ala
1               5                   10                  15

Ala Thr Ala Cys Thr Cys
            20
```

5. The method of claim 1, wherein a fecal specimen of the autistic subject prior to administration comprises *Clostridium perfringens* that is free of a *Clostridium perfringens* alpha-toxin gene.

6. The method of claim 1, wherein a fecal specimen of the autistic subject prior to administration comprises *Clostridium perfringens* that comprises a *Clostridium perfringens* beta2-toxin gene and a *Clostridium perfringens* alpha-toxin gene but is free of a *Clostridium perfringens* beta-toxin gene, a *Clostridium perfringens* epsilon-toxin gene, and a *Clostridium perfringens* iota-toxin gene.

7. The method of claim 1, wherein a fecal specimen of the autistic subject prior to administration comprises *Clostridium perfringens* that comprises a *Clostridium perfringens* beta2-toxin gene but is free of a *Clostridium perfringens* alpha-toxin gene, a *Clostridium perfringens* beta-toxin gene, a *Clostridium perfringens* epsilon-toxin gene, and a *Clostridium perfringens* iota-toxin gene.

8. The method of claim 1, wherein the autistic subject is a subject having early onset autism.

9. The method of claim 1, wherein the autistic subject is a subject having late onset autism.

10. The method of claim 1, wherein the autistic subject is a subject having regressive autism.

11. The method of claim 1, wherein the autistic subject is a child less than 12 years of age.

12. The method of claim 1, wherein the autistic subject is a child 3 years of age or younger.

13. The method of claim 1, wherein the presence of the beta2-toxin-gene-positive *Clostridium perfringens* in the fecal sample is detected with a primer pair direct to sense and anti-sense strands of beta2-toxin-gene-positive *Clostridium perfringens*.

14. The method of claim 1, wherein the anti-toxin is an antibody against a toxin, and wherein the antibody is a neutralizing antibody, an inhibitory antibody, a polyclonal antibody, a monoclonal antibody, an antigen-binding fragment of an antibody, or a bispecific antibody.

15. The method of claim 14, wherein the antigen-binding fragment comprises a Fab antibody fragment, a F(ab')$_2$ antibody fragment, a Fv antibody fragment, or a single chain variable fragment (scFv).

16. The method of claim 1, further comprising administering a probiotic.

* * * * *